United States Patent [19]
Morgan

[11] Patent Number: 4,905,679
[45] Date of Patent: Mar. 6, 1990

[54] BONE FRACTURE REDUCTION DEVICE AND METHOD OF INTERNAL FIXATION OF BONE FRACTURES

[75] Inventor: Frank H. Morgan, Woodland Hills, Calif.

[73] Assignee: M P Operation, Inc., Woodland Hills, Calif.

[21] Appl. No.: 158,686

[22] Filed: Feb. 22, 1988

[51] Int. Cl.$^4$ .............................................. A61F 5/04
[52] U.S. Cl. .................................................... 606/70
[58] Field of Search ................ 128/92 C, 92 D, 92 B, 128/92 EB, 92 R, 92 YP

[56] References Cited

U.S. PATENT DOCUMENTS

| | | | |
|---|---|---|---|
| 1,105,105 | 7/1914 | Sherman | 128/92 YP |
| 4,429,690 | 2/1984 | Angelino-Pievani | 128/92 YP |
| 4,444,181 | 4/1984 | Wevers et al. | 128/92 YP |
| 4,683,878 | 8/1987 | Carter | 128/92 YP |

FOREIGN PATENT DOCUMENTS

| | | | |
|---|---|---|---|
| 2386301 | 12/1978 | France | 128/92 YP |
| 2472373 | 7/1981 | France | 128/92 YP |
| 611147 | 5/1979 | Switzerland | 128/92 YP |

OTHER PUBLICATIONS

Vitallium Surgical Appliances, Sherman-Type Plates, Mar. 1948.
Sherman Stainless, 1943.
Lane's Steel Bone-Plates.

*Primary Examiner*—Robert A. Hafer
*Assistant Examiner*—Charles H. Sam
*Attorney, Agent, or Firm*—Philip D. Junkins

[57] ABSTRACT

A bone fracture reduction device for the internal fixation and immobilization of bone fragments. The device is comprised of at least two spaced bone affixation plate sections formed of bio-compatible metallic material and at least one leg section of like bio-compatible metallic material interconnecting each pair of the plate sections. Each plate section has at least one screw hole extending therethrough for receiving a bone screw to be driven into a bone fragment and each leg section is of relatively narrow width with respect to the width of the plate sections. The device is affixed via its plate sections to adjacent bone fragments with each leg section spanning a fracture line. Each leg section is deformable after affixation of its connected pair of plate sections to adjacent bone fragments whereby upon kinking deformation thereof the distance between each connected pair of plate sections is reduced and the adjacent bone fragments are compressed to close the fracture line between such plate sections and immobilize the fracture.

7 Claims, 1 Drawing Sheet

BONE FRACTURE REDUCTION DEVICE AND METHOD OF INTERNAL FIXATION OF BONE FRACTURES

BACKGROUND OF THE INVENTION

A bone fracture is a traumatic disruption of the continuity of a bone. If there is relative motion of the bone fragments at the fracture site irritation of the surrounding tissues and heavy pain ensue and the time of fracture healing is usually extended. Proper rejoinder of bone fragments is thus dependent upon immobilization of the fracture site. Classically, bone fragment reduction (bone fragments properly aligned and abutted along the fracture line) and immobilization for fractured limb bones has been accomplished by external limb casts. Such casts must be worn for long periods of time, are heavy and unbalancing to the body skeletal structure and muscular system, inhibit bone vascularity (promotes fast and effective bone healing), and may result in bone resorption because of the total absence of tensile and compressive functional loading throughout the fractured bone structure. Fractures in bones other than the arms and legs are more difficult to immobilize and the use of exterior casts may not be possible.

Over the past twenty years the use of compression plate techniques for internal fixation of fractures have been developed and widely applied. With internal fixation, by means of bone screws and compression plates (particularly plates made of biocompatible metals and metal alloys (such as titanium and stainless steel), immediate and absolute immobilization is achieved through interfragmentary compression. Other materials and devices such as wires, intramedullary nails or externally fixed pins are used mainly to reduce bone fracture mobility and improve the position of the fracture segments. The aim of internal bone fracture fixation is to allow early, pain-free movement of the injured limb, mandible, etc., thus avoiding the consequences of long lasting immobilization, i.e., bone fracture disease, bone resorption, etc.

With internal bone fixation it is important that the application of the compression plate or fracture reduction device result in relative immobility of the bone fragments and tight closure of the fracture interface. Without such immobility and tight closure, changing tension and compression loads tend to produce relative motion between the fracture fragments with resultant undesirable fragment shortening due to bone resorption. Through the proper use of a bio-compatible metallic fracture reduction device (a surgically applied implant), static forces applied as interfragmentary compression by the device prevent relative motion between the fracture surfaces. Thus, compressive pre-loading of the bone fragments (through the compression device) prevents relative motion at the fracture site in spite of functional use of the limb, mandible, etc., without external immobilization or splinting. With mechanical stimuli (forces and motion permitted via the internal bone fixation technique, rapid and healthy healing of the fracture is promoted and bone vascularity is maintained and restored. Vascularity of bone is interrupted by the fracture trauma and by surgical intervention (application of the compression device) but revascularization is restored and enhanced by the rigid immobilization of the bone fragment or fracture interfaces through internal fixation techniques.

During the early application of compression device techniques, the devices were meant to be merely fixed to the bone fragments of the fracture for alignment purposes. Later, the value of interfragmentary compression, through devices and plates applied under tension, was recognized. A number of internal fixation devices have been developed with built-in compression devices—devices for tensioning the device or plate to create interfragmentary compression. Some of such systems have required that the plate-tensioning device remain implanted with the plate. Other systems have been designed with removable plate-tensioning apparatus.

Further developments in compression plate designs and attachment screws (also formed of bio-compatible metals and metal alloys) have related to screw head and screw hole geometry, i.e., conical geometry of the screw shoulder and oval screw holes in the compression plate for promoting bone fragment compression during screw application. Attempts to obtain optimal stability of fixation have most recently resulted in the use of congruent fitment between screw and screw hole including both conical counter-sunk screw holes and hemicylindrical screw holes.

Numerous problems remain in the application of the various compression plate systems that are commercially available for internal bone fixation. Some systems require great care in the installation of bone screws so that their orientation is always perpendicular to the plate. When contouring a plate to fit a curved bone surface, circularly fitting screw holes may become distorted and cause high friction against screw rotation or may completely inhibit a screw from entering the screw hole. Built-in tensioning devices associated with some compression plates increase the number of crevices between opposed metal surfaces and promote metal corrosion. Removable plate tensioning devices necessitate generally wider (size) and longer (time) surgical exposure. Buckling or kinking of the bone fragments at the fracture line may occur as a result of improper tensioning at the end of the compression plate during plate application.

In U.S. Pat. No. 4,441,181 granted to H. S. Wevers et al there has been disclosed a bone clip for the surgical repair of bones with the clip having body portions with spaced parallel connecting legs at each side thereof. The clip is designed for use in surgically straightening a bone. A V-notch is cut into the bone and pin holes are drilled into the bone on each side of the notch to receive legs depending from the body portions of the clip at each end thereof. After insertion of the clip legs into the pin holes, the spaced parallel legs are deformed inwardly so as to draw the legs together towards each other to force closure of the V-notch cut into the bone and thereby straighten such bone. The Wevers et al bone clip provides no positive connection of the clip to the bone as by threaded bone screws and there is no elongated support to the bone so as to avoid flexure because there is only one connection point of the clip (depending leg) on each side of the cut V-notch.

Applicant of the present invention, in U.S. patent application Ser. No. 07/069,644 filed July 6, 1987 and entitled "Bone Fracture Reduction Plate and Method of Internal Fixation of Bone Fractures," has disclosed a bone compression plate (formed of bio-compatible metal or metal alloy) provided in its central portion with a compression adjustment aperture of ovate configuration. During application of the compression plate to a bone fracture, the adjustment aperture in the plate is situated over the fracture line and the plate (at each side of the fracture line) is secured to the bone sections on each side of the fracture line by bone screws. The combination of the plate and screws comprises an internal compression fixation system. To tension the plate and thereby apply compression forces or loading to the fracture interface of the bone fragments, transverse spreading forces are applied to the parallel legs of the adjustment aperture of the plate with the result that such legs are permanently deformed (bent) outwardly and the compression plate is reduced in its length thereby forcing the bone fragments into high compression interface relationship along with strong immobilization of the bone fragments. The compression plate design disclosed in U.S. application Ser. No. 07/069,644 offers significant advantages with respect to bone repair and healing, including: full closure of the fracture line and maintenance of interface compression; no requirement of a built-in plate tensioning device or use of removable tensioning apparatus; short term of the surgical intervention for installation of the compression plate with minimal bone exposure and time of bone exposure; no remaining bone gaps; and no buckling or kinking of the bone fragments at the fracture line because of improper tensioning.

It is a principal object of the present invention to provide a unique bone fracture reduction device of relatively small but effective structure for use in internal fixation of fractures.

It is a further object of the invention to provide a bone fracture device for use in the internal reduction and fixation of bone fractures, which may be rapidly and easily installed over a bone fracture or multiplicity of fracture lines and adjusted in place to completely close the one or more fractures and apply appropriate compression loads to the fracture fragments.

It is still a further object of the invention to provide a bone fracture strapping device, for use in the internal fixation of bone fractures and immobilization of the fracture fragments, which may be installed over a bone fracture or interconnected system of bone fractures during short-term surgical intervention and adjusted (after affixation to the bone fracture fragments) to accomplish fracture line closure and apply appropriate compression loads to the fracture fragments to promote rapid bone healing.

It is yet another object of the present invention to provide a unique method for surgical internal fixation of bone fractures and immobilization of the fracture fragments to promote rapid bone healing.

Other objects and advantages of the invention will be apparent from the following summary and detailed description of the bone fracture reduction device of the invention and of the internal bone fixation methodology of the invention taken together with the accompanying drawing figures.

SUMMARY OF THE INVENTION

The present invention relates to an improved bone fracture reduction device for use in the internal fixation of bone fractures and immobilization of the fracture fragments and to the improved method for surgical internal fixation of bone fractures via utilization of such reduction device. The bone fracture reduction device of the invention, formed of a bio-compatible metal or metal alloy such as titanium or stainless steel, has a size and configuration dependent upon the size and arrangement of the bone fragments requiring internal fixation and immobilization. The bone fracture reduction device is relatively small and has particular application to the reduction of a bone fracture or multiple related fractures of the human skull or cranium.

The reduction device of the invention, in one of its important embodiments, is of thin plate construction and is configured with two like bone affixation end portions interconnected by a narrow central leg portion. The end portions of the device each contain two (or more) screw holes all in general alignment with the interconnecting leg portion. The bone fracture reduction device is held in place by bone screws set into abutting bone fragments with the leg portion of the device extending across the fracture line between such fragments. After affixation of the reduction device to the abutting bone fragments, the relatively thin and narrow central leg portion of the device is kinked to reduce the effective length of the leg portion to thereby create a tension force through the leg portion to the end portions of the device which are affixed to the bone fragments. Such tension force thereby creates a compression force or loading to the fracture interface of the bone fragments with the result that the fracture is reduced and immobilized.

In alternative configurations, the bone fracture reduction strapping device of the invention may be provided with two or more interconnecting leg portions capable of being kinked (to reduce their effective length) after affixation of the two or more connected end portions of the device to abutting bone fragments requiring reduction and immobilization. Where two or more interconnecting leg portions comprise part of the bone fracture reduction device, the device is provided with an intermediate bone affixation portion or plate including at least one screw hole through which a bone screw is set into a bone fragment of the fracture system requiring reduction and immobilization. Thus, the bone fracture reduction device may take the overall shape of the letter "L" (see FIG. 4) to reduce and close an arcuate fracture line or two intersecting fracture lines. Further, the bone fracture reduction device may take the overall shape of the letter "Y" (see FIG. 5) to reduce and close a more complex system of fracture lines between abutting bone fragments. Other configurations of the fracture reduction device of the invention are illustrated in FIGS. 6 and 7.

The bone fracture reduction device in design, and the methodology of internal bone fracture fixation, of the invention offer significant advantages with respect to bone repair and healing, including: full closure of the fracture line and maintenance of interface compression: no requirement of a built-in tensioning device or use of removable tensioning apparatus; short term of the surgical intervention for installation of the bone fracture reduction device with minimal bone exposure and time of open bone exposure; no remaining bone gaps; and no buckling or kinking of the bone fragments at the fracture line or lines because of improper tensioning.

BRIEF DESCRIPTION OF THE DRAWING FIGURES

Figures 1, 2, 3:
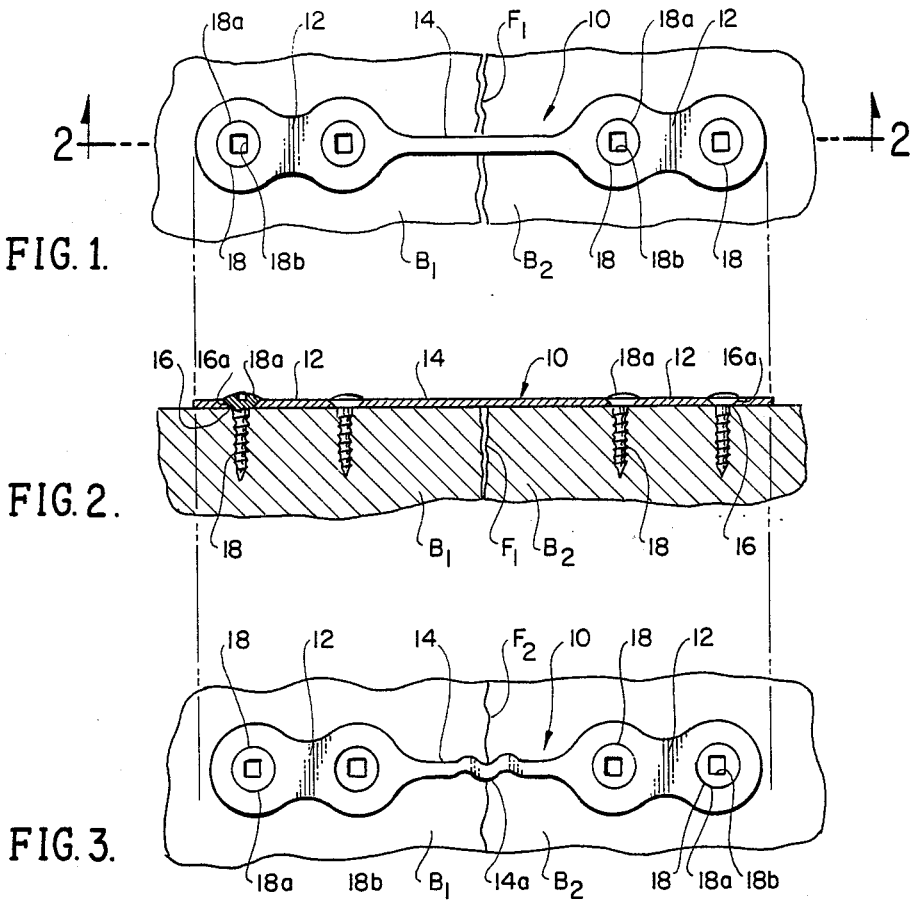
FIG. 1 is an oversized top plan view of a bone fracture reduction device in accordance with the present invention in place over an area of bone fracture before reduction of the fracture by the fracture reduction device.
FIG. 2 is a longitudinal side sectional view of the reduction device and fractured bone area of FIG. 1 taken along line 2—2 of FIG. 1.

FIG. 3 is a top plan view of the bone fracture area and bone fracture reduction device of FIG. 1 showing the shape of the reduction device after kinking and final internal fixation and closure of the fracture; and FIGS. 4–7 are oversized top plan views of four alternative forms of bone fracture reduction devices in accordance with the present invention with fracture lines illustrated in dotted line fashion.

DETAILED DESCRIPTION OF THE INVENTION

Referring to FIGS. 1 and 2 of the drawing sheet, there is illustrated a bone fracture reduction device 10 in accordance with the invention with the device 10 in place over an area of bone $B_1$–$B_2$ presenting an open fracture line $F_1$ (bone fragment interface). The bone fracture reduction device 10 is fabricated from a plate of relatively thin bio-compatible (stress free) metal or metal alloy and configured with two like bone affixation end plates or sections 12 interconnected by a central relatively narrow leg section 14. The end plate sections 12 of device 10 each contain two (or more) screw holes 16 (including top counter-sinks 16a) with the screw holes of each end section in general alignment with the screw holes of the opposite end section and in alignment with the long axis of the interconnecting leg section 14. As shown in FIGS. 1 and 2, the bone fracture reduction device 10 is held in place over bone area $B_1$–$B_2$, across open fracture line $F_1$, by bone screws 18. Preferably the screw hole counter-sinks 16a in the end sections 12 of device 10 are conical in shape and interface with the hemispherical lower surface portion of the screw heads 18a so that when each screw is set in bone through a screw hole 16, the screw head 18a and hole countersink 16a interface in tight congruent fitment.

As shown in FIGS. 1 and 2 the screw heads 18a are provided with a square wrenching recess 18b. Alternatively, the screw heads may be provided with a slotted head or a head having an "Allen" type wrench recess or a "Torx" type (six point star) wrench recess. As previously indicated, the bone screws to be utilized with the bone fracture reduction device of the present invention are made of bio-compatible metal or metal alloys and preferably have self-tapping screw type threads with a screw body having little or no taper along its principal length. A pilot hole, matched to the minor diameter of the screw, must be drilled in the bone for each bone screw with careful attention directed to the avoidance of thermal damage to the bone.

In accordance with bone fracture reduction devices and bone reduction methodology of the invention, there is shown in FIG. 3 the fracture reduction device 10 after kinking deformation of the narrow leg section 14 of the device with the result that the length of the device is reduced thereby compressing the bone fragments $B_1$ and $B_2$ at their interface with closure of the fracture line $F_2$. The kinked area of leg section 14 is shown as 14a in FIG. 3. In surgical application of the internal bone fracture reduction methodology of the invention, kinking of the interconnecting leg section 14 of the device 10 (after the device has been secured to the bone fragments presenting the open fracture line) may be accomplished by the use of "Aderer" type pliers commonly used by orthodontists for kinking wires connecting orthodontic band to increase the tension forces applied by such wires to such bands. This type of plier has two prongs on one side and one prong on the opposing side of the plier jaws. Kinking deformation of the leg section 14 of the device 10 may also be accomplished by "needle nose" type pliers of well-known design.

Armamentarium (tools) utilized to accomplish internal bone fracture fixation, in accordance with the invention, should have working parts and surfaces of the same bio-compatible metal or metal alloy so as to avoid foreign metal contamination of the bone fracture reduction device 10 and screws 18 of the fixation system. Thus, for example, titanium faced screw drivers, pliers, wrenches, bone drills, screw hole reamers, etc. are recommended for use with bone fracture reduction devices and bone screws of bio-compatible titanium.

EXAMPLE

A bone fracture reduction device 10, of the type illustrated in FIGS. 1–3, has been fabricated from unalloyed commercially pure titanium with a yield strength in the range of 30,000 to 40,000 psi. The device was utilized to reduce and immobilize a fracture in the maxilla of a patient with the device having a thickness of 1 mm and an overall length (before application) of 28 mm. The interconnecting narrow central leg section of the device had a width of 1 mm and a length of 6.8 mm and the end bone affixation plates or sections of the device had a maximum width of 4.6 mm. After application of the device across the open fracture line with affixation to the bone fragments of the maxilla by titanium bone screws having round heads with a Torx type wrench recess, the central leg section of the device was kinked by an "Aderer" type plier with the result that the overall length of the device was reduced to 27 mm and the fracture line in the maxilla was appropriately closed and the abutting bone fragments immobilized.

Figure 4:
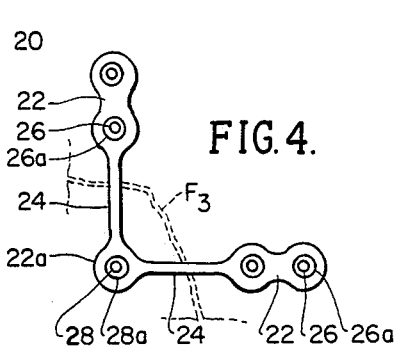

In FIG. 4 there is illustrated an alternative form of the bone fracture reduction device of the invention, i.e., a bone fracture reduction device 20 having the general shape of the letter "L". This configuration of the device of the invention may be used to reduce and close an arcuate open fracture (a fracture $F_3$ as illustrated in dashed line fashion in FIG. 4) or two intersecting open fractures. The "L" shaped device 20 includes two like bone affixation end plates or sections 22, each interconnected by a relatively narrow leg section 24 to an intermediate bone affixation plate or section 22a. The end sections 22 of device 20 each contain two (or more) screw holes 26 (including top counter-sinks 26a) with the screw holes of each end section in alignment with the long axis of the leg section 24 interconnecting such end section to the intermediate bone affixation section 22a. The intermediate affixation section 22a includes at least one screw hole 28 (with counter-sink 28a). To close the arcuate open fracture $F_3$ (after appropriate affixation of the "L" shaped device 20 to the adjacent bone fragments by bone screws each of the legs 24 may be kinked, to a relatively more or less extent, to close the fracture line and provide immobility to the bone fragments.

Figure 5:
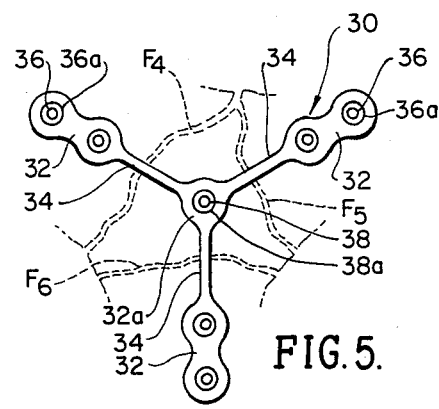

In FIG. 5 there is illustrated a further alternative form of the bone fracture reduction device of the invention, i.e., a reduction device 30 having the general shape of the letter "Y". This configuration of the device of the invention may be used to reduce and close a more complex system of open fracture lines between adjacent bone fragments. A complex system of open fracture lines $F_4$–$F_6$ is illustrated by dashed line representation in FIG. 5. The "Y" shaped device 30 includes three like bone affixation plates or sections 32, each interconnected by a relatively narrow leg section 34 to an intermediate or hub bone affixation plate or section 32a. The end sections 32 of the device 30 each contain two (or more) screw holes 36 (including top counter-sinks 36a) with the screw holes of each end section in alignment with the long axis of the leg section 34 interconnecting such end section to the intermediate bone affixation section 32a. The intermediate affixation section 32a includes at least one hole 38 (with counter-sink 38a). To close the open fractures $F_4$–$F_6$ (after appropriate affixation of the "Y" shaped device 30 to the adjacent bone fragments by bone screws) each of the legs 34 may be kinked, to a relatively more or less extent, to close the fracture lines and provide immobility to the bone fragments in the area of the fracture site.

Figure 6:
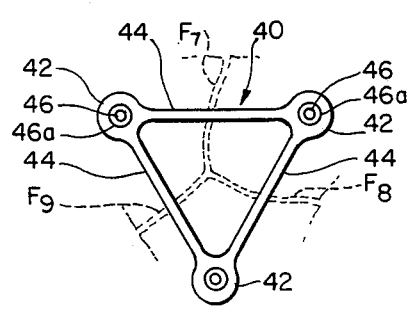
Figure 7:
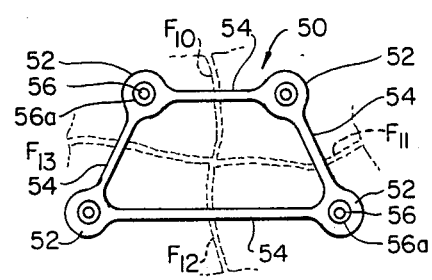

Two additional alternative configurations of bone fracture reduction devices within the scope of the present invention are shown in FIGS. 6 and 7. The device 40 of FIG. 6 includes three like bone affixation plates or sections 42 arranged in spaced equilateral triangular configuration with interconnecting leg sections 44. Each affixation plate 42 includes one central screw hole 46 (with counter-sink 46a). A complex system of open fracture lines $F_7$–$F_9$ is illustrated by dashed line representation in FIG. 6. The device 50 of FIG. 7 includes four like bone affixation plates 52 arranged in spaced trapezoidal configuration with interconnecting leg sections 54. Each plate 52 includes one central screw hole 56 (with counter-sink 56a). A complex system of open fracture lines $F_{10}$–$F_{13}$ is illustrated by dashed line representation in FIG. 7.

It is to be understood that further alternative configurations of the bone fracture reduction device, in accordance with the invention, have been fabricated. Also, it should be apparent that in numerous surgical bone repair situations, the intermediate narrow leg sections of the reduction device may be present to some degree to better fit the abutting bone fragment configurations and/or the fracture line orientations.

Through use of the bone fracture reduction devices of the present invention for the internal fixation of bone fractures and immobilization of bone fracture fragments, and through the practice of the improved method of surgical internal fixation of bone fractures via utilization of such devices, faster and more effective rejoinder and healing of fractured bone fragments may be achieved. Shorter term surgical intervention and bone exposure is accomplished. Heavy and awkward external casts and splinting devices are frequently not required, long-term bone immobilization is avoided, and pain-free early use of the injured bone area can be achieved.

While the invention has been described in connection with particular structural embodiments of the bone fracture reduction devices and method of internal fixation of bone fractures, many modifications of the invention will be apparent to those skilled in the art. Accordingly, such modifications are to be included within the spirit and scope of the invention as defined by the following claims.

What I claim is:

1. A bone fracture reduction device for the internal fixation and immobilization of bone fragments at one or more bone fracture sites comprising:

(a) two or more spaced bone affixation plate sections formed of bio-compatible metallic material and arranged as one or more pairs of plate sections, each of said plate sections having at least one screw hole extending therethrough for receiving a bone screw to be driven into a bone fragment on one side of a bone fracture site to affix each of said plate sections to such bone fragment; and (b) one leg section of like bio-compatible metallic material interconnecting each pair of plate sections, each leg section being less than half the width of the plate sections to which it is connected and being of uniform cross section throughout its length and each leg section spanning a fracture line between its respective connected pair of plate sections upon affixation of said plate sections to adjacent bone fragments at a fracture site, and each leg section being deformable after affixation of its connected par of plate sections to adjacent bone fragments whereby upon kinking deformation thereof the distance between each connected pair of said plate sections is reduced and the adjacent bone fragments compressed to close the fracture line between said plate sections and immobilize the fracture.

2. A bone fracture reduction device for the internal fixation and immobilization of bone fragments as claimed in claim 1 wherein said device includes two bone affixation plate sections with at least two screw holes extending therethrough and the screw holes of each of said plate sections are in general alignment with the long axis of the leg section of said device which interconnects said plate sections.

3. A bone fracture reduction device for the internal fixation and immobilization of bone fragments as claimed in claim 1 wherein said device includes two terminal bone affixation plate sections with at least two screw holes extending therethrough, an intermediate bone affixation plate section having a single screw hole extending therethrough, and two leg sections with each of said leg sections interconnecting one of said terminal plate sections to said intermediate plate section to form two pairs of plate sections to the bone fracture reduction device.

4. A bone fracture reduction device for the internal fixation and immobilization of bone fragments as claimed in claim 3 wherein the two leg sections of said device are oriented at an acute, right or obtuse angle with respect to one another.

5. A bone fracture reduction device for the internal fixation and immobilization of bone fragments as claimed in claim 1 wherein said device includes three or more bone affixation plate sections with at least two screw holes extending therethrough, a central hub-type bone affixation plate section having a single screw hole extending therethrough, and a leg section interconnecting each of said terminal plate sections with said central plate section to form three or more pairs of plate sections of the bone fracture reduction device.

6. A bone fracture reduction device for the internal fixation and immobilization of bone fragments as claimed in claim i wherein said device includes three or more like bone affixation plate sections arranged as three or more pairs of said plate sections with each of said plate sections having at least one screw hole extending therethrough, each of said pairs of plate sections interconnected by a leg section of equal or unequal length with respect to the leg sections of adjacent like pairs of plate sections whereby said device takes on the form of a closed multiple sided geometrical plane figure.

7. A bone fracture reduction device for the internal fixation and immobilization of bone fragments as claimed in claim 1 wherein each bone affixation plate section and each interconnecting leg section are fabricated of a bio-compatible metal or metallic alloy selected from the group consisting of titanium, titanium alloys, cobalt-chrome alloys and stainless steel.

* * * * *